(12) United States Patent
Culjat et al.

(10) Patent No.: US 8,690,331 B2
(45) Date of Patent: Apr. 8, 2014

(54) CORNEAL HYDRATION SENSING SYSTEM

(75) Inventors: Martin Culjat, Los Angeles, CA (US); Priyamvada Tewari, Los Angeles, CA (US); Jean L. Bourges, Paris (FR); Jean P. Hubschman, Los Angeles, CA (US); Rahul S. Singh, Palo Alto, CA (US); Zachary Taylor, Poway, CA (US); Warren S. Grundfest, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/597,947

(22) Filed: Aug. 29, 2012

(65) Prior Publication Data

US 2013/0162949 A1 Jun. 27, 2013

Related U.S. Application Data

(60) Provisional application No. 61/528,558, filed on Aug. 29, 2011.

(51) Int. Cl.
*A61B 3/10* (2006.01)

(52) U.S. Cl.
USPC .. 351/221; 351/220; 351/159.73; 351/159.78

(58) Field of Classification Search
USPC ............................... 351/159.04, 159.78, 220
See application file for complete search history.

(56) References Cited

U.S. PATENT DOCUMENTS 6,592,574 B1 * 7/2003 Shimmick et al. ................. 606/4
7,641,343 B1 * 1/2010 Motamedi et al. ............ 351/221
7,828,438 B1 * 11/2010 Motamedi et al. ............ 351/221
2010/0110381 A1 * 5/2010 Motamedi et al. ............ 351/221
2012/0087970 A1 * 4/2012 Newman ........................ 424/427
2013/0012803 A1 * 1/2013 Guimera Brunet et al. .. 600/383

OTHER PUBLICATIONS

Wilmink GJ, Ibey BL, Tongue T, et al; Development of a compact terahertz time-domain spectrometer for the measurement of the optical properties of biological tissues. J. Biomed. Opt. 0001;vol. 16(4):047006-047006-10 (Apr. 2011).*

* cited by examiner

*Primary Examiner* — Evelyn A Lester
*Assistant Examiner* — William Alexander
(74) *Attorney, Agent, or Firm* — Venable LLP; Henry J. Daley

(57) ABSTRACT

A corneal hydration sensing system includes an illumination system configured to provide an illumination beam of terahertz radiation, an optical system arranged in an optical path of the illumination system to relay and direct at least a portion of the illumination beam of terahertz radiation onto a cornea of a subject and to receive at least a portion of terahertz radiation reflected from the cornea to provide a return beam of terahertz radiation, and a detection system arranged in an optical path of the return beam of terahertz radiation. The detection system is configured to provide a detection signal from detecting at least a portion of the return beam of terahertz radiation. The corneal hydration sensing system also includes a signal processing system configured to communicate with the detection system to receive the detection signal. The signal processing system processes the detection signal to provide a measure of an amount of hydration sensed in the cornea of the subject.

25 Claims, 2 Drawing Sheets

CORNEAL HYDRATION SENSING SYSTEM

CROSS-REFERENCE OF RELATED APPLICATION

This application claims priority to U.S. Provisional Application No. 61/528,558 filed Aug. 29, 2011, the entire contents of which are hereby incorporated by reference.

This invention was made with Government support of Grant No. W81XWH-09-2-0017, awarded by the Department of Defense, and Grant No. ECCS-0801897, awarded by the National Science Foundation. The Government has certain rights in this invention.

BACKGROUND

1. Field of Invention

The field of the currently claimed embodiments of this invention relates to systems and methods for sensing corneal hydration, and more particularly to systems and methods for sensing corneal hydration using terahertz illumination.

2. Discussion of Related Art

Corneal hydration is currently approximated in the clinic by extrapolation using the central corneal thickness (CCT) measurements. These methods are based on ultrasound or optical pachymetry and assume a linear relationship between the CCT and the average water content of the eye. This relationship was established from the empirical fit of 11 healthy human corneas from a cornea bank. No correlation statistics are given, but deviations of 20% or greater are seen in the data, and the linear fit predicts a dehydrated corneal thickness of ~90 micrometers, when values of ~200 micrometers are reported in the literature. Furthermore, the extrapolation is based upon healthy corneas and this approach also cannot provide accurate analysis for changes relating to disease states in cornea. Even if these fits could be improved by increasing the number of samples, extrapolation of corneal hydration from CCT based on samples from the population cannot account for physiological variations between people, including geriatric and pediatric cases. An additional complication to the current state of the art is that most clinical methods for measuring corneal thickness in vivo are themselves modified by changes in hydration. Hydration changes in the cornea significantly modify the speed of sound and the refractive index of the tissue thus further reducing the accuracy of ultrasound and optical pachymetry.

Remote measurement of corneal hydration has also been demonstrated using confocal Raman spectroscopy, which can study the OH and CH bonds in a material by illuminating it with monochromatic laser radiation and collecting scattered light. However, the scattering yield is typically $10^{-6}$ to $10^{-8}$ and the excitation illumination fluence necessary to achieve accurate measurements exceeds the ANSI regulations for use in humans by orders of magnitude.

Therefore, pachymetry methods offer very accurate thickness measurements but the mapping from thickness to hydration is very inaccurate. Thus ophthalmologic pachymetry is limited by inherent constraints and no amount of system or methodological improvements can overcome these limitations. Therefore, there remains a need for improved systems for sensing corneal hydration.

SUMMARY

A corneal hydration sensing system according to some embodiments of the current invention includes an illumination system configured to provide an illumination beam of terahertz radiation, an optical system arranged in an optical path of the illumination system to relay and direct at least a portion of the illumination beam of terahertz radiation onto a cornea of a subject and to receive at least a portion of terahertz radiation reflected from the cornea to provide a return beam of terahertz radiation, and a detection system arranged in an optical path of the return beam of terahertz radiation. The detection system is configured to provide a detection signal from detecting at least a portion of the return beam of terahertz radiation. The corneal hydration sensing system also includes a signal processing system configured to communicate with the detection system to receive the detection signal. The signal processing system processes the detection signal to provide a measure of an amount of hydration sensed in the cornea of the subject.

A method of sensing corneal hydration according to some embodiments of the current invention includes illuminating a cornea of a subject with terahertz radiation, detecting at least a portion of the terahertz radiation reflected from the cornea, and determining an amount of hydration in at least a portion of the cornea of the subject based on reflected terahertz radiation detected.

BRIEF DESCRIPTION OF THE DRAWINGS

Further objectives and advantages will become apparent from a consideration of the description, drawings, and examples.

DETAILED DESCRIPTION

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

An ideal clinical system for measuring corneal hydration should be non-invasive, non-contact to prevent irritation of the corneal tissue and risk of contamination or infection, deposit minimal energy, and measure the changes in hydration directly. THz corneal hydration sensing and imaging according to an embodiment of the current invention meets these requirements. THz imaging is non-contact and typical illumination powers are 2-3 orders of magnitude lower than the quoted ANSI standard for the 0.01 THz to 0.1 THz range. THz imaging is also robust to user error since the methodology does not require precise positioning and application of pressure by the user as does ultrasonic and optical pachymetry.

The term "terahertz radiation" is intended to refer to electromagnetic radiation with the frequency range of 0.1 THz to 10 THz.

The terms "optical system", "optical component", etc. are intended to include optical components, etc. that are suitable for functioning with terahertz radiation.

Terahertz imaging and sensing measures water content directly and thus measurements can be made on the microsecond time scale. This is sufficiently fast to integrate into refractive laser procedures in the eye—such as LASIK—for online hydration adjustment of the beam, for example. Furthermore, because of the small spot size and large standoff, the beam can be scanned quickly to generate a complete hydration-map image of the cornea instead of a point measurement (pachymetry is a point measurement with no scanning capability). This is useful for measuring injury and disease extents such as in traumatic injury, stromal edema, or dystrophy.

Figure 1:
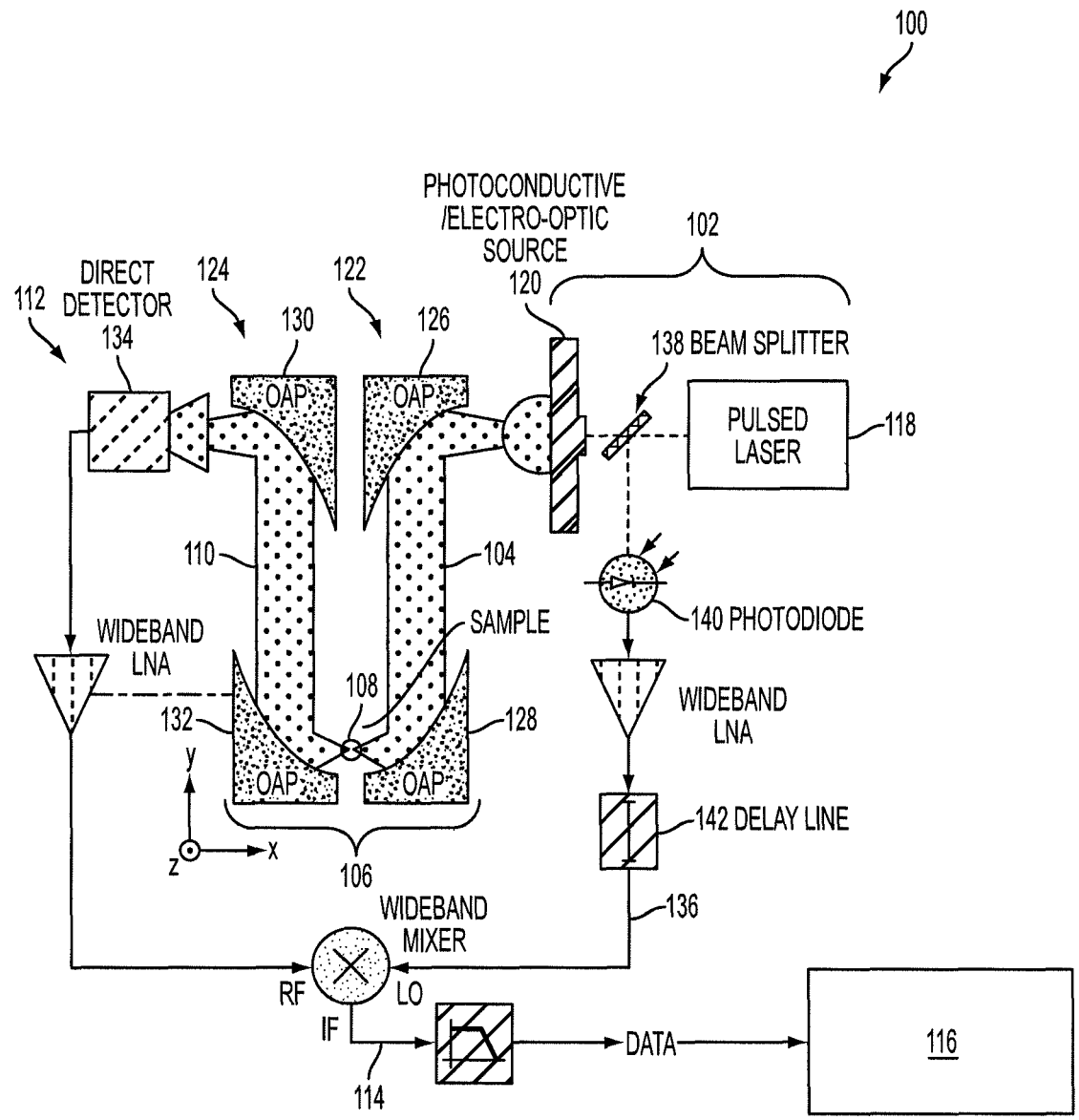
FIG. 1 is a schematic illustration of a corneal hydration sensing system according to an embodiment of the current invention.

FIG. 1 provides a schematic illustration of a corneal hydration sensing system 100 according to an embodiment of the current invention. The corneal hydration sensing system 100 includes an illumination system 102 configured to provide an illumination beam of terahertz radiation 104, and an optical system 106 arranged in an optical path of the illumination system 102 to relay and direct at least a portion of the illumination beam of terahertz radiation 104 onto a cornea 108 of a subject and to receive at least a portion of terahertz radiation reflected from the cornea 108 to provide a return beam of terahertz radiation 110. The corneal hydration sensing system 100 also includes a detection system 112 arranged in an optical path of the return beam of terahertz radiation 110. The detection system is configured to provide a detection signal 114 from detecting at least a portion of the return beam of terahertz radiation 110. The corneal hydration sensing system 100 also includes a signal processing system 116 configured to communicate with the detection system 112 to receive the detection signal 114. The signal processing system 116 processes the detection signal 114 to provide a measure of an amount of hydration sensed in the cornea 108 of the subject.

The signal processing system 116 can be hard-wired or wireless to communicate with the detection system 112. The signal processing system can be a specialized component, such as, but not limited to ASICs and/or FPGAs, and/or a programed general-purpose device such as a computer. Such a computer can be a work station, a desk top computer, a lap top computer, a hand held computer, and/or a networked computer or computers. In addition, the signal processing system 116 can be connected to any available input/output devices and/or storage devices according to the particular application. The signal processing system 116 is configured to calculate at least relative corneal hydration between at least two portions of the subject's cornea 108 based on the detection signal 114. In some embodiments, the signal processing system 116 can be further configured to calculate a corneal hydration image of the subject's cornea 108 based on the detection signal 114.

In some embodiments, as is illustrated in FIG. 1, the illumination system 102 can include an ultrafast pulsed near infrared (NIR) laser 118 and a photoconductive switch (PCS) 120 to generate broad band terahertz illumination in the range of 100 GHz-1 THz, for example. However, the broad concepts of the current invention are not limited to this particular source of terahertz radiation.

In some embodiments, the optical system 106 can include an illumination optical 122 system configured to provide oblique-angle illumination of terahertz radiation of the subject's cornea 108 and a pick-up optical system 124 configured to provide the return beam of terahertz radiation. However, the invention is not limited to only oblique-angle illumination. Other embodiments can include orthogonal, or near orthogonal illumination by selecting appropriate optical components. In some embodiments, the illumination optical system 122 can include a pair of off-axis parabolic mirrors (126, 128) and the pick-up optical system 124 can include a pair of off-axis parabolic mirrors (130, 132). Alternatively, or in addition, lens components can be used in the illumination and/or pick-up optical system. The lens components can be refractive optical elements, diffractive optical elements and/or graded refractive index elements, depending on the particular application. The broad concepts of the current invention are not limited to only the particular arrangement of optical components illustrated in the embodiment of FIG. 1. Additional and/or different components may be used depending on the particular application. An embodiment of the current invention uses a series of off-axis parabolic mirrors and Teflon lenses (THz optics) to collimate and focus the THz illumination on the cornea. The reflected THz illumination is collected by an additional set of THz optics and focused to the detection system 112.

In an embodiment, the detection system 112 includes a feedhorn of a zero-bias schottky diode detector 134. Diode rectifiers can also be packaged in ways that don't use a waveguide or feedhorn in alternative embodiments. In this embodiment, the illumination is rectified by the diode detector 134 and then mixed with a reference signal 136 using a balanced, RF mixer. In this example, the reference signal 136 (Local Oscillator) is provided by splitting off a portion of the pulsed laser beam with beam splitter 138, generating an electrical signal with a photodiode 140, followed by a delay line 142. The DC output of the mixer is normalized by a reference value and then used as a reflectivity value. This value is converted to a hydration by volume percentage using the known terahertz electromagnetic properties of the corneal tissue and water.

In an embodiment, the NIR laser optics, NIR laser, photoconductive switch, THz optics, and THz detector can all be mounted together in one rigid fixture. The fixture can be scanned quickly over the patient's eye using a combination of linear stages and gimbal mounts, for example, to create a curvilinear path. In some embodiments, the detection system is configured to detect the return beam of terahertz radiation within a frequency band of about 0.1 THz to about 0.7 THz.

Absolute point values and/or hydration images or maps can be obtained by calibrating the acquired data. The calibrations can be empirical, can be based on predetermined models, or can be semi-empirical models that include information from a specific subject, for example. Empirical values for cornea thickness and/or curvature can be included in a semi-empirical model for calibrating the measurements, for example. However, the concepts of the current invention are not limited to only this example.

Figure 2:
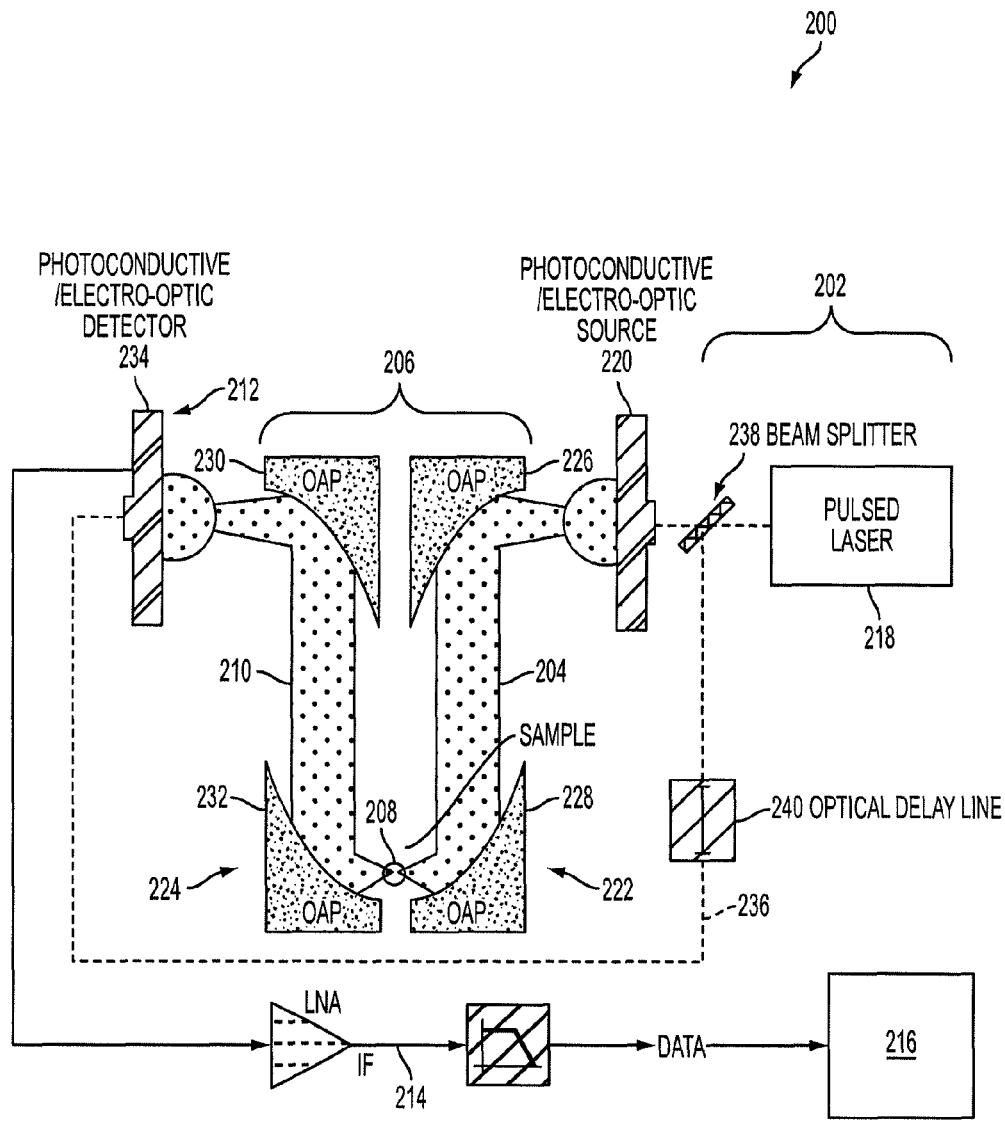
FIG. 2 is a schematic illustration of a corneal hydration sensing system according to another embodiment of the current invention.

FIG. 2 provides a schematic illustration of a corneal hydration sensing system 200 according to another embodiment of the current invention. The corneal hydration sensing system 200 includes an illumination system 202 configured to provide an illumination beam of terahertz radiation 204, and an optical system 206 arranged in an optical path of the illumination system 202 to relay and direct at least a portion of the illumination beam of terahertz radiation 204 onto a cornea 208 of a subject and to receive at least a portion of terahertz radiation reflected from the cornea 208 to provide a return beam of terahertz radiation 210. The corneal hydration sensing system 200 also includes a detection system 212 arranged in an optical path of the return beam of terahertz radiation 210. The detection system is configured to provide a detection signal 214 from detecting at least a portion of the return beam of terahertz radiation 210. The corneal hydration sensing system 200 also includes a signal processing system 216 configured to communicate with the detection system 212 to receive the detection signal 214. The signal processing system 216 processes the detection signal 214 to provide a measure of an amount of hydration sensed in the cornea 208 of the subject.

The signal processing system 216 can be hard-wired or wireless to communicate with the detection system 212. The signal processing system can be a specialized component, such as, but not limited to ASICs and/or FPGAs, and/or a programed general-purpose device such as a computer. Such a computer can be a work station, a desk top computer, a lap top computer, a hand held computer, and/or a networked computer or computers. In addition, the signal processing system 216 can be connected to any available input/output devices and/or storage devices according to the particular application. The signal processing system 216 is configured to calculate at least relative corneal hydration between at least two portions of the subject's cornea 208 based on the detection signal 214. In some embodiments, the signal processing system 216 can be further configured to calculate a corneal hydration image of the subject's cornea 208 based on the detection signal 214.

In some embodiments, as is illustrated in FIG. 2, the illumination system 202 can include an ultrafast pulsed near infrared (NIR) laser 218 and a photoconductive switch (PCS) 220 to generate broad band terahertz illumination in the range of 100 GHz-1 THz, for example. However, the broad concepts of the current invention are not limited to this particular source of terahertz radiation.

In some embodiments, the optical system 206 can include an illumination optical 222 system configured to provide oblique-angle illumination of terahertz radiation of the subject's cornea 208 and a pick-up optical system 224 configured to provide the return beam of terahertz radiation. The illumination optical system 222 can include a pair of off-axis parabolic mirrors (226, 228) and the pick-up optical system 224 can include a pair of off-axis parabolic mirrors (230, 232). The broad concepts of the current invention are not limited to only this particular arrangement of optical components. Additional and/or different components may be used depending on the particular application. An embodiment of the current invention uses a series of off-axis parabolic mirrors and Teflon lenses (THz optics) to collimate and focus the THz illumination on the cornea. The reflected THz illumination is collected by an additional set of THz optics and focused to the detection system 212.

In an embodiment, the detection system 212 includes a photoconductive or electro-optic detector 234. In this embodiment, the photoconductive or electro-optic detector 234 is used to detect the return beam reflected by the subject's cornea. The time domain system has an optical delay line 140 that allows synchronous, time lapsed gating of the return beam resulting in sampling of the electric field of the return beam. The peak of the return beam signal, or area under the curve for a specific portion of the spectrum can be used in a signal processing system to generate hydration data. In this example, the reference optical signal 236 is provided by splitting off a portion of the pulsed laser beam with beam splitter 238, followed by the optical delay line 140.

The cornea is composed of ~78% water by volume with the remaining 22% composed almost entirely of collagens. Collagen is nearly transparent in the THz spectral region with a very low index of refraction. Water has a very large THz refractive index and loss tangent. Thus, small changes in corneal hydration equate to large changes in THz reflectivity. The penetration depth and hydration sensitivity can be tuned based on the clinicians need by selecting the effective operational band of the imager. Currently we use a detector centered at 100 GHz for deep layer imaging and a detector centered at 600 GHz for shallower layer imaging.

To build a practical system that is compact, low-cost, and high-bandwidth, a THz imager can be made according to an embodiment of the current invention using a broad band source such as a frequency multiplier chain or PCS that is stable under the rapid motion associated with scanning. A triplet of detectors operating at 100 GHz, 300 GHz, and 600 GHz can be mounted in the system for simultaneous acquisition of shallow to deep measurements, for example. The detectors can all be coupled to low noise amplifiers (LNAs) and broad band mixers and DC values can be simultaneously acquired with a low noise ADC.

A station with padding conformable to a patient's face can be set up and the THz system scanned quickly in front of the patients stationary eyes. A microcontroller can transform reflected signal strength directly to hydration by volume and this can be outputted to the screen.

A working prototype has been built. We have used this prototype system to obtain hydration-sensitive data and imagery in many test targets such as paper, polypropylene towels, as well as body tissues such as healthy and diseased skin. We have also imaged corneas in a variety of configurations and hydration states. We have quantified the relationship between corneal hydration and terahertz reflectivity in ex vivo corneas and built a terahertz imaging system capable of scanning the curved surface of the eye. We have obtained measurements in a live rabbit model, and demonstrated that this technology is capable of resolving 0.18% changes in the water concentration of the cornea in vivo. We have also successfully completed a preliminary in vivo animal trial consisting of 8 rabbit corneas. Results show statistically significant changes in THz reflectivity over the hydration range of 78%-81%. The results also suggest a ~3× increase in dynamic range over ultrasound based pachymetry.

Some embodiments of the current invention use THz illumination to detect and image hydration in the cornea in vivo. The methodology according to an embodiment of the current invention centers around a broad band THz source spanning the range of 100 GHz to 1 THz. The THz illumination can be generated with a photoconductive switch, frequency multiplier source, or diode, or elctro-optic source, and collimated and focused by THz optics (off-axis parabolic mirrors or dielectric lenses) onto the surface of the cornea, according to an embodiment of the current invention. The reflected THz illumination is collected by a second set of THz optics and focused into the feedhorn of a diode detector mounted in a rectangular waveguide. The waveguide can be chosen to limit the detection bandwidth to a specific band. The output of the diode detector is sent to a receiver consisting of an LNA and RF mixer. The resulting DC voltage is then recorded as a raw pixel value and is a direct measurement of the cornea THz power reflectivity. Using the known dielectric properties of corneal tissue and the assumed axial hydration gradient of the cornea, the measured reflectivity is converted to a hydration percentage (percent water by volume). Two detectors can be employed. One sensitive to 100 GHz illumination and one sensitive to 600 GHz illumination. The 100 GHz band provides deeper penetration but lower spatial resolution. The 600 GHz band provides higher spatial resolution but lower depth of penetration. Both detectors can be utilized at the same time with the appropriate THz dichroic filter. The THz optics, source, and detector can all be rigidly attached to one unit. This unit can be swept in front of the patient's stationary eyes in a curvilinear arc to form an image.

THz imaging and sensing measures water content directly and thus measurements can be made on the microsecond time scale. This is sufficiently fast to integrate into refractive laser procedures in the eye—such as LASIK—for online hydration dependent adjustment of the beam intensity. Refractive correction errors in LASIK can be attributed to incorrect ablation rate setting based on erroneous estimates of corneal hydration. Furthermore, because of the small spot size and large standoff, the beam can be scanned quickly to generate a complete hydration-map image of the cornea instead of a point measurement (pachymetry is a point measurement with no scanning capability). In addition to uses in conjunction with laser surgery of the eye, this can also be useful for measuring injury and disease extents such as in traumatic injury, stromal edema, or dystrophy, for example. For example, THz hydration imaging of the cornea can be useful for:

Fuch's Dystrophy
Ocular trauma assessment
Corneal graft rejection
Keratoconus
Ablation control in LASIK procedures Currently, corneal hydration is approximated in the clinic by extrapolation using the central corneal thickness (CCT) measurements. These methods are based on ultrasound or optical pachymetry and assume a linear relationship between the CCT and the average water content of the eye. This relationship was established from the empirical fit of 11 healthy human corneas from a cornea bank. No correlation statistics are given, but deviations of 20% or greater are seen in the data, and the linear fit predicts a dehydrated corneal thickness of 90 micrometers, when values of 200 micrometers are reported in the literature. Furthermore, the extrapolation is based upon healthy corneas and this approach cannot provide accurate analysis for changes relating to disease states in cornea. Even if these fits could be improved by increasing the number of samples, extrapolation of corneal hydration from CCT based on samples from the population cannot account for physiological variations between people, including geriatric and pediatric cases. An additional complication to the current state of the art is most clinical methods for measuring corneal thickness in vivo are themselves modified by changes in hydration. Hydration changes in the cornea significantly modify the speed of sound and the refractive index of the tissue thus further reducing the accuracy of ultrasound and optical pachymetry. To summarize, pachymetry methods offer very accurate thickness measurements but the mapping from thickness to hydration is very inaccurate. Thus ophthalmologic pachymetry is limited by inherent constraints and no amount of system or methodological improvements can overcome these limitations. THz imaging measures hydration directly and in principle is only limited by the signal-to-noise ratio (SNR) of the system yielding measurements that are on the order of 10× more sensitive than pachymetry.

The THz source can be any source that provides ~1 THz of illumination bandwidth. Photoconductive source, diode multipliers, backward wave oscillators, resonant tunneling diodes, and any other source with sufficient output bandwidth can be used. Similarly, a range of detectors may provide sufficient capability including pyroelectric detectors, bolometers, golay cells, photoconductors, or electro-optics.

According to some embodiments of the current invention, a more powerful source and/or more sensitive detector can allow a faster image acquisition time. An array of THz detectors can improve the system's reception of return signals from curved surfaces and allow faster acquisition time. A beam scanning system can allow for a stationary THz source and patient and significantly improve acquisition time.

Further examples are described in the priority application of the current application, U.S. Provisional Application No. 61/528,558 filed Aug. 29, 2011, the entire contents of which are hereby incorporated by reference for all purposes. However, the broad concepts of the current invention are not limited to these particular examples.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A corneal hydration sensing system, comprising:
an illumination system configured to provide an illumination beam of terahertz radiation;
an optical system arranged in an optical path of said illumination system to relay and direct at least a portion of said illumination beam of terahertz radiation onto a cornea of a subject and to receive at least a portion of terahertz radiation reflected from said cornea to provide a return beam of terahertz radiation;
a detection system arranged in an optical path of said return beam of terahertz radiation, said detection system configured to provide a detection signal from detecting at least a portion of said return beam of terahertz radiation; and
a signal processing system configured to communicate with said detection system to receive said detection signal,
wherein said signal processing system processes said detection signal to provide a measure of an amount of hydration sensed in said cornea of said subject.

2. A corneal hydration sensing system according to claim 1, wherein said signal processing system is configured to calculate at least relative corneal hydration between at least two portions of said subject's cornea based on said detection signal.

3. A corneal hydration sensing system according to claim 1, wherein said signal processing system is configured to calculate at least relative corneal hydration between a portion of said subject's cornea for at least two different times based on said detection signal.

4. A corneal hydration sensing system according to claim 2, wherein said signal processing system is configured to calculate at least one of a corneal hydration image or a corneal hydration map of said subject's cornea based on said detection signal.

5. A corneal hydration sensing system according to claim 4, wherein said detection system is configured to detect said return beam of terahertz radiation within a frequency band of about 0.1 THz to about 10 THz.

6. A corneal hydration sensing system according to claim 4, wherein said detection system is configured to detect said return beam of terahertz radiation within a frequency band of about 0.1 THz to about 0.7 THz.

7. A corneal hydration sensing system according to claim 4, wherein said signal processing system is configured to calibrate said corneal hydration image to provide an absolute hydration image of said subject's cornea.

8. A corneal hydration sensing system according to claim 7, wherein said signal processing system is configured to calibrate said corneal hydration image using a predetermined model.

9. A corneal hydration sensing system according to claim 7, wherein said signal processing system is configured to calibrate said corneal hydration image using a semi-empirical model that incorporates patient-specific information.

10. A corneal hydration sensing system according to claim 1, wherein said signal processing system is configured to calculate a point value that is an absolute corneal hydration for at least one local region or an overall average of said subject's cornea based on said detection signal.

11. A corneal hydration sensing system according to claim 10, wherein said detection system is configured to detect said return beam of terahertz radiation within a frequency band of about 0.1 THz to about 0.7 THz.

12. A corneal hydration sensing system according to claim 10, wherein said signal processing system is configured to calibrate said corneal hydration image using a predetermined model.

13. A corneal hydration sensing system according to claim 10, wherein said signal processing system is configured to calibrate said corneal hydration image using a semi-empirical model that incorporates patient-specific information.

14. A corneal hydration sensing system according to claim 4, wherein said signal processing system is further configured to calculate a point value that is an absolute corneal hydration for at least one local region or an overall average of said subject's cornea based on said detection signal.

15. A corneal hydration sensing system according to claim 14, wherein said detection system is configured to detect said return beam of terahertz radiation within a frequency band of about 0.1 THz to about 10 THz to provide a first detection signal to said signal processing system to calculate a corneal hydration image of said subject's cornea based on said first detection signal, and
wherein said detection system is configured to detect said return beam of terahertz radiation within a frequency band of about 0.1 THz to about 0.7 THz to provide a second detection signal to said signal processing system to calculate a point value that is an absolute corneal hydration for at least one local region or an overall average of said subject's cornea based on said second detection signal.

16. A corneal hydration sensing system according to claim 14, wherein said detection system is configured to detect said return beam of terahertz radiation within a frequency band of about 0.1 THz to about 0.7 THz to provide a first detection signal to said signal processing system to calculate a corneal hydration image of said subject's cornea based on said first detection signal, and
wherein said wherein said detection system is configured to detect said return beam of terahertz radiation within a frequency band of about 0.1 THz to about 0.7 THz to provide a second detection signal to said signal processing system to calculate a point value that is an absolute corneal hydration for at least one local region or an overall average of said subject's cornea based on said second detection signal.

17. A corneal hydration sensing system according to claim 1, wherein said optical system comprises an illumination optical system configured to provide oblique-angle illumination of terahertz radiation of said subject's cornea, and
wherein said optical system further comprises a pick-up optical system configured to provide said return beam of terahertz radiation.

18. A corneal hydration sensing system according to claim 17, wherein said illumination optical system comprises a pair of off-axis parabolic mirrors, and
wherein said pick-up optical system comprises a pair of off-axis parabolic mirrors.

19. A corneal hydration sensing system according to claim 16, wherein said optical system comprises an illumination optical system configured to provide oblique-angle illumination of terahertz radiation of said subject's cornea, and
wherein said optical system further comprises a pick-up optical system configured to provide said return beam of terahertz radiation.

20. A corneal hydration sensing system according to claim 19, wherein said illumination optical system comprises a pair of off-axis parabolic mirrors, and
wherein said pick-up optical system comprises a pair of off-axis parabolic mirrors.

21. A method of sensing corneal hydration, comprising:
illuminating a cornea of a subject with terahertz radiation;
detecting at least a portion of said terahertz radiation reflected from said cornea; and
determining an amount of hydration in at least a portion of said cornea of said subject based on reflected terahertz radiation detected.

22. A method of sensing corneal hydration according to claim 21, wherein said determining an amount of hydration in at least a portion of said cornea of said subject comprises determining relative corneal hydration between at least two portions of said cornea.

23. A method of sensing corneal hydration according to claim 21, wherein said determining an amount of hydration in at least a portion of said cornea of said subject comprises generating a corneal hydration image of said cornea.

24. A method of sensing corneal hydration according to claim 23, wherein said generating said corneal hydration image of said cornea comprise calibrating said corneal hydration image to provide an absolute hydration image of said subject's cornea.

25. A method of sensing corneal hydration according to claim 24, wherein said calibrating comprises using a predetermined model.

* * * * *